United States Patent
Ostrovska

(10) Patent No.: US 11,034,580 B2
(45) Date of Patent: Jun. 15, 2021

(54) METHOD FOR TUMOR DETECTION AND TARGETED HYPERTHERMIA

(71) Applicant: Lyubov Ostrovska, Reisterstown, MD (US)

(72) Inventor: Lyubov Ostrovska, Reisterstown, MD (US)

(73) Assignee: Lyubov Ostrovska, Reisterstown, MD (US)

(*) Notice: Subject to any disclaimer, the term of this patent is extended or adjusted under 35 U.S.C. 154(b) by 0 days.

(21) Appl. No.: 16/726,892

(22) Filed: Dec. 25, 2019

(65) Prior Publication Data

US 2020/0140269 A1 May 7, 2020

Related U.S. Application Data

(63) Continuation of application No. 13/459,900, filed on Apr. 30, 2012, now abandoned.
(Continued)

(51) Int. Cl.
*B82Y 5/00* (2011.01)
*A61K 41/00* (2020.01)
(Continued)

(52) U.S. Cl.
CPC ............ *B82Y 5/00* (2013.01); *A61K 41/0052* (2013.01); *A61K 49/1863* (2013.01);
(Continued)

(58) Field of Classification Search
CPC .. B82Y 5/00; A61N 2/00–12; A61K 41/0052; C12N 5/0663
See application file for complete search history.

(56) References Cited

U.S. PATENT DOCUMENTS

2005/0090732 A1* 4/2005 Ivkov .................. A61N 2/002
   600/411
2009/0169478 A1* 7/2009 Leuschner ............... B82Y 5/00
   424/9.3

(Continued)

*Primary Examiner* — Thaddeus B Cox
(74) *Attorney, Agent, or Firm* — Wilson Sonsini Goodrich & Rosati

(57) ABSTRACT

The present invention provides stem cells loaded with bi-functional magnetic nanoparticles (nanoparticle-loaded stem cells (NLSC)) that both: a) heat in an alternating magnetic field (AMF); and b) provide MRI contrast enhancement for MR-guided hyperthermia. The nanoparticles in the NLSC are non-toxic, and do not alter stem cell proliferation and differentiation, the nanoparticles do however, become heated in an alternating magnetic field, enabling therapeutic applications for cancer treatment. Due to the fact that circulating stem cells home to tumors and metastasis, and participate in neovascularization of growing tumors, the NLSC of the present invention allows tracking of the tissue distribution of infused stem cells and selective heating of targeted tissues with AMF. NLSC can deliver hyperthermia to hypoxic areas in tumors for sensitization of those areas to subsequent treatment, thus delivering therapy to the most treatment-resistant tumor regions. The heating of diseased tissue either results in direct cell killing or makes the tumor more susceptible to radio- and/or chemotherapy. The targeted hyperthermia provided by the present invention has clinical potential because it is associated with fewer side effects, and can also be used in combination with conventional treatment modalities, significantly enhancing their effectiveness. The NLSC of the present invention can be used for MR image-guided hyperthermia in oncology, in stem cell research for cell tracking and heating, and for elimination of mis-injected stem cells.

17 Claims, 7 Drawing Sheets

Related U.S. Application Data

(60) Provisional application No. 61/480,468, filed on Apr. 29, 2011.

(51) Int. Cl.
*C12N 5/0775* (2010.01)
*A61N 5/10* (2006.01)
*A61K 49/18* (2006.01)
A61K 35/12 (2015.01)

(52) U.S. Cl.
CPC ............ *A61K 49/1896* (2013.01); *A61N 5/10* (2013.01); *C12N 5/0663* (2013.01); *A61K 2035/124* (2013.01); *C12N 2529/00* (2013.01)

(56) References Cited

U.S. PATENT DOCUMENTS

| | | | |
|---|---|---|---|
| 2010/0303730 A1* | 12/2010 | Hegmann | A61K 49/1836 424/9.32 |
| 2012/0157824 A1* | 6/2012 | Bossmann | C12Q 1/37 600/420 |
| 2012/0277517 A1* | 11/2012 | Ivkov | A61N 1/406 600/2 |

* cited by examiner

METHOD FOR TUMOR DETECTION AND TARGETED HYPERTHERMIA

REFERENCE TO RELATED APPLICATIONS

This application is a continuation application of U.S. patent application Ser. No. 13/459,900, filed on Apr. 30, 2012, now abandoned, which application claims the benefit of U.S. Provisional Patent Application No. 61/480,468, filed on Apr. 29, 2011, each of which is hereby incorporated by reference for all purposes as if fully set forth herein.

STATEMENT OF GOVERNMENTAL INTEREST

This invention was made with U.S. government support under NIEHS grant no. P30 ES00319. The U.S. government has certain rights in the invention.

BACKGROUND OF THE INVENTION

Magnetic Iron oxide nanoparticles (MION) are increasingly used for clinical applications, such as magnetic resonance imaging (MRI), drug delivery, and hyperthermia. Injection of magnetic fluids (MION suspensions) into tumors and their subsequent heating in an alternating magnetic field (AMF) has been developed as a cancer treatment, resulting in direct tumor cell killing or making the cells more susceptible to radiation- or chemotherapy.

Targeted hyperthermia has clinical potential because it is associated with fewer side effects, and it can also be used in combination with conventional treatment modalities. Despite promising results, hyperthermia has not yet been established in the clinic because technological limitations preclude selective deposition of heat to the tumor, especially to treatment resistant hypoxic areas.

One of the many challenges in biomedicine is to deliver treatment at the right place, at the right dose, and at the right time. This requires advances in diagnostics and imaging, and would benefit from new modalities of treatment including targeted hyperthermia. In this context, stem cells loaded with magnetic nanoparticles (designed to heat) can serve as thermotherapeutic agents that deliver heat to the sites of neovascularization in growing tumors. Targeted stem cell-based delivery of nanoparticles (NP) offers the potential to minimize toxicity when compared to systemic intravenous administration of the thermotherapeutic agents.

Targeted treatment delivery requires monitoring. Monitoring the location and migration of grafted cells is essential for understanding their interaction within the host and their therapeutic effects. Magnetic resonance imaging allows for noninvasive stem cell (SC) tracking in tissues. Bi-functional nanoparticles with enhanced magnetic properties allow for stem cell MR imaging and heating. This can be used for therapeutic purposes and for elimination of mis-injected stem cells.

There continues to exist an unmet need for better targeted therapies for cancer and related diseases, and for better MR contrast agents.

SUMMARY OF THE INVENTION

In accordance with an embodiment, the present invention provides the use of NP that become heated in AMF for magnetic resonance imaging (MRI). Use of bi-functional nanoparticles allows tracking the tissue distribution of infused NP and nanoparticle loaded stem cells (NLSC). The magnetic NP with enhanced MR properties, and which become heated in AMF enables therapeutic applications of NLSC of the present invention.

In accordance with an embodiment, the present invention provides a method for treatment of cancer in a subject comprising: a) obtaining NLSC comprising a bi-functional nanoparticle; b) administering to the subject, an effective amount of the NLSC; c) allowing sufficient time for the NLSC to localize to the tumor; d) detecting the NLSC in the tumor by imaging the tumor through MRI; and/or e) applying a sufficient amount of an AMF to the subject such that the NP within the NLSC will heat the tumor in the subject when exposed to an AMF and sensitize the tumor to further treatment; and f) administering an effective amount of a pharmaceutical composition comprising one or more chemotherapeutic agents.

In accordance with another embodiment, the present invention provides a method for treatment of cancer in a subject comprising: a) obtaining NLSC comprising a bi-functional nanoparticle; b) administering to the subject, an effective amount of the NLSC; c) allowing sufficient time for the NLSC to localize to the tumor; d) detecting the NLSC in the tumor by imaging tumor through MRI; and/or e) applying a sufficient amount of an AMF to the subject such that the NLSC will heat the tumor in the subject when exposed to an AMF and sensitize the tumor to further treatment; and f) administering an effective amount of radiotherapy to the tumor.

In accordance with a further embodiment, the present invention provides a method for treatment of cancer in a subject comprising: a) obtaining NLSC comprising a bi-functional nanoparticle; b) administering to the subject, an effective amount of the NLSC; c) allowing sufficient time for the NLSC to localize to the tumor; d) detecting the NLSC in the tumor by imaging the tumor through MRI; and/or e) applying a sufficient amount of an AMF to the subject such that the NLSC will heat the tumor in the subject when exposed to an AMF and sensitize the tumor to further treatment; f) administering an effective amount of a pharmaceutical composition comprising one or more chemotherapeutic agents; and g) administering an effective amount of radiotherapy to the tumor.

In accordance with a yet another embodiment, the present invention provides the use of NLSC for treatment of a tumor in a subject comprising: a) obtaining NLSC comprising a bi-functional nanoparticle; b) administering to the subject, an effective amount of the NLSC; c) allowing sufficient time for the NLSC to localize to the tumor; d) detecting NLSC in the tumor by imaging tumor through MRI; and/or e) applying a sufficient amount of an AMF to the subject such that the NLSC will heat the tumor in the subject when exposed to an alternating magnetic field and sensitize the tumor to further treatment.

DETAILED DESCRIPTION OF THE INVENTION

Figure 1A:
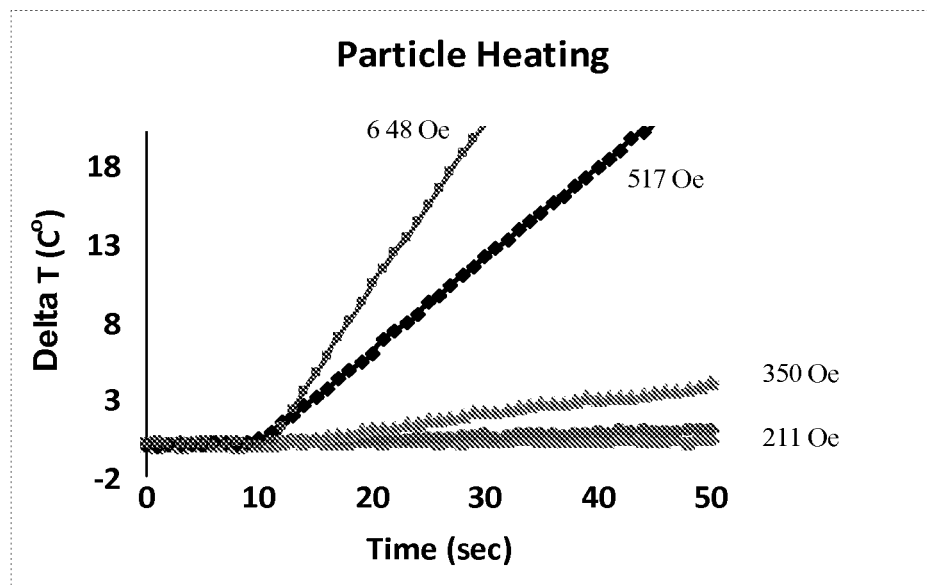
FIG. 1A is a graph depicting the heat output of the BNF particles as a function of magnetic field strength. (Oe-magnetic field amplitude in Oersteds).

In accordance with an embodiment, the present invention provides NLSC comprising a bi-functional nanoparticle, which have unique heating characteristics, and which generate localized heating when in the presence of an AMF and can be imaged with magnetic resonance imaging. The NLSC of the present invention are useful in sensitizing primary or metastatic tumors of a subject to chemotherapy and radiotherapy.

The present invention shows that NLSC-based delivery of nanoparticles allows for effective targeting of nanoparticles to tumors. Targeted delivery of infused particles to tumors is necessary to decrease the risk of under-treating cancerous tissue and over-heating normal adjacent structures. Stem cell-based delivery of nanoparticles, as provided herein increases the effectiveness of cancer thermotherapy, chemotherapy and radiotherapy, and improves specific tumor uptake, distribution, and retention time of magnetic nanoparticles in tumors compared to other methods of nanoparticle distribution.

The present invention allows for cancer hyperthermia with magnetic nanoparticles (i.e. magnetic nanoparticles can generate heat when exposed to AMF depending upon its amplitude), as either a stand-alone or adjuvant therapy for metastatic cancer. Because metastatic cancer is a systemic condition comprising multiple lesions (tumors) that are hypoxic, and therefore refractory to standard therapies, new and targeted treatment technologies are under investigation.

The methods provided herein is the combined use of magnetic nanoparticles that are targeted to tumor cells with a stem cell, e.g., a mesenchymal stem cell, which are recruited by the tumor to aid in vascularizing the hypoxic regions localized deep in the tumor mass, and which allows for selective accumulation of the nanoparticles at the deep interior of tumors following administration. After allowing sufficient time for localization post-injection of the NLSC, the patient is subjected to a non-injurious AMF for a period of time. The AMF will cause the nanoparticles to heat locally while minimizing heating to untargeted areas. The rate of heat output, or power loss (also known as specific absorption rate, defined as Watts/g material) of the nanoparticles depends upon the AMF properties.

AMF-NP interactions cause direct tissue heating in a frequency- and amplitude-dependent manner that is not selective to tissue type. The challenge is to provide sufficient amplitude or power of AMF at a fixed frequency to extract therapeutic heat from the magnetic nanoparticles and simultaneously minimize the non-specific power deposition to avoid overheating and damaging normal tissue.

As used herein, the term "nanoparticle loaded stem cells" or (NLSC) are stem cells which can be of autologous or allogeneic origin. Stem cells are distinguished from other cell types by two important characteristics. First, they are unspecialized cells capable of renewing themselves through cell division, sometimes after long periods of inactivity. Second, under certain physiologic or experimental conditions, they can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions. More importantly, circulating stem cells home to tumors and metastasis, and participate in neovascularization of growing tumors.

In accordance with an embodiment, the NLSC can be autologous stem cells. Autologous stem cells are preferred to ascertain that cells transplanted into a patient are not recognized as foreign by the patient's immune system and rejected. Autologous stem cells can be derived: a) from circulation (endothelial progenitor cells), b) from bone marrow (BM), c) can be obtained from cell banks (including stem cells from amniotic fluid, umbilical cord, cord blood, placenta, and autologous human embryonic stem cell (hESC) lines if available).

In accordance with another embodiment, the NLSC can also be allogenic stem cells. Allogenic stem cells can be utilized in case of patient's bone marrow failure after cancer treatment, and if no autologous cells from a stem cell bank are available. Autologous stem cells can be derived from non-embryonic tissues ("adult" stem cells) and from hESC lines from in vitro fertilization (IVF) embryos (human pluripotent cell lines, iPSC, trans-differentiated SC from different tissues, including gut, liver, fat, and other tissues).

In accordance with yet another embodiment, the NLSC of the present invention are mesenchymal stem cells. These cells are also known as bone marrow stromal stem cells or skeletal stem cells by some. These non-hematopoietic stem cells make up a small proportion of the stromal cell population in the bone marrow, and can generate bone, cartilage, fat, cells that support the formation of blood, and fibrous connective tissue. Most cancer patients have increased level of circulating BM-derived SC in the bloodstream. In response to cytokine signaling from growing tumor, bone marrow stem cells migrate to tumor, differentiate into endothelial progenitor cells, and participate in tumor neovasculogenesis.

Neovascularization is essential for the growth of solid tumors. Understanding the pathways of tumor vascularization helps develop improved strategies for anti-angiogenic therapy. Accumulating evidence confirms incorporation of circulating bone-marrow derived progenitor cells or endothelial precursor cells (EPC) into tumor vasculature.

In accordance with one or more embodiments of the present invention, the inventors have demonstrated that mesenchymal stem cells are incorporated into cancer tumors with active vessel formation and appear to play a significant role in tumor neovascularization. The present inventors have also confirmed that noninvasive MRI technology can be utilized to monitor homing and progression of MSC in tumors.

In accordance with an embodiment of the present invention, the medicament for treating a disease in a subject can encompass many different formulations known in the pharmaceutical arts, including, for example, intravenous and sustained release formulations. With respect to the inventive methods, the disease can include cancer. Cancer can be any cancer, including any solid tumor type, such as alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, colon cancer, esophageal cancer, cervical cancer, gastrointestinal carcinoid tumor, hypopharynx cancer, kidney cancer, larynx cancer, liver cancer, lung cancer, malignant mesothelioma, melanoma, nasopharynx cancer, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

The term "diseased tissue" may also refer to tissue or cells of the immune system, such as tissue or cells effected by AIDS, pathogen-borne diseases, which can be bacterial, viral, parasitic, or fungal. Examples of pathogen-borne diseases include HIV, tuberculosis, and malaria; hormone-related diseases, such as obesity, vascular system diseases, central nervous system diseases, such as multiple sclerosis, and undesirable matter, such as adverse angiogenesis, restenosis, amyloidosis, toxic reaction by-products associated with organ transplants, and other abnormal cell or tissue growth.

In accordance with an embodiment, the stem cells used in the NLSC of the methods of the present invention are autologous, i.e., derived from the subject being treated.

In accordance with another embodiment, the stem cells used in the NLSC of the methods of the present invention are allogenic, i.e. derived from a donor having a similar genetic background and species, including, for example, a family-related donor.

The NLSC of the present invention can be isolated from the subject to be treated, or allogeneic donor, and expanded in cell culture, using methods known in the art, until sufficient quantities of cells are obtained.

As used herein, the term "bi-functional nanoparticle" means that the nanoparticle has two or more different functions. In an embodiment, the nanoparticles of the NLSC of the present invention comprise magnetic nanoparticles which can be detected and visualized using magnetic resonance imaging (MRI), and these particles are also capable of heating via being placed in an alternating magnetic field (AMF). The nanoparticles should be magnetic or superparamagnetic in character. Examples include magnetic iron oxides $Fe_3O_4$ (magnetite) and $\gamma$-$Fe_2O_3$ (maghemite) which have been proved to be well tolerated by the human body.

The nanoparticles of the invention may be metal or metal oxide nanoparticles and may for example contain cobalt, iron, cobalt and platinum or gold. The nanoparticles should be biocompatible or, at least, be of an acceptable level of toxicity at therapeutic dosage levels. Preferably, the nanoparticles used in the methods of the invention are iron oxide nanoparticles. In one embodiment of the invention, the nanoparticles are magnetic nanoparticles. Magnetic nanoparticles that can be used in the invention include ferromagnetic, or superparamagnetic nanoparticles. Preferably, the magnetic nanoparticles are superparamagnetic iron oxide (SPIO) nanoparticles.

In an embodiment, the nanoparticles of the present invention comprise bionized nanoferrite (BNF) particles prepared via the core-shell method with a core of 75-80% (w/w) magnetite and a shell of hydroxyethyl starch, and which are available with particle diameters of about 80 nm and 100 nm.

In an embodiment of the methods of the present invention, the magnetic nanoparticles contained within the NLSCs can be heated to cause stem cell and tumor cell death. The heating of the nanoparticles is typically carried out by exposing the NLSC to an AMF inducing inductor which is used to energize the nanoparticles. Preferably, the AMF inducing inductor is a resonant circuit device incorporated or embodied within an MRI apparatus. Alternatively, the AMF inducing device may be a separate apparatus.

Other functions in addition to imaging and heating are also contemplated by the nanoparticles of the present invention. The nanoparticles can be labeled with other imaging agents, such as radionuclides, such as positron emitters, like $^{18}F$ or $^{11}C$. Fluorescent labeling and functionalizing the nanoparticles with monoclonal antibodies are also contemplated herein, and are well within the skill of those in the art.

The term "localization" as used herein, means that the NLSC of the present invention have sufficient time post-administration, to migrate through the tissues or the body of the subject and arrive at the site of neovascularization of the tumor or tumors. These areas of localization are typically hypoxic and are generally resistant to chemotherapy and radiotherapy.

In accordance with an embodiment, the time to allow the NLSC to localize to the tumor site is between about 3 days to about 10 days, preferably between about 5 to about 7 days.

The term "detection" as used herein, means that the NLSC of the present invention are scanned with a magnetic resonance imaging (MRI) device or machines which are known and available in the art. The whole body of the subject or the local area where the tumor is suspected of being located is placed in the MRI machine and the nanoparticles loaded on the stem cells are detected in the machine and their location is identified. Preferably, iron oxide nanoparticles are contained within the NLSC, and MRI is used to detect the iron oxide nanoparticles. The types of MRI that may be used include $T_1$ weighted scans, $T_2$ weighted scans and $T_2^*$ weighted scans. The MRI may be used to measure hypointensity and/or hyperintensity.

In accordance with one or more embodiments of the methods of the present invention, the heating of NP is carried out by an AMF-inducing inductor. An AMF is a magnetic field that changes the direction of its field vector periodically, typically, in a sinusoidal, triangular, rectangular, or similarly shaped pattern, with a frequency in the range of from about 80 kHz to 800 kHz. An AMF may also be added to a static magnetic field, such that only the AMF component of the resulting magnetic field vector changes direction. An AMF may be accompanied by an alternating electric field and may be electromagnetic in nature. The AMF strength administered to the subject is between about 500 Gauss to about 1500 Gauss, and the magnetic field amplitude of the AMF is between about 5 Oersteds (Oe) to about 600 Oe.

In accordance with one or more embodiments of the methods of the present invention, ionizing radiation or radiotherapy is used in post-administration of the NLSC of the present invention as part of a combination therapy for the treatment of a tumor. The type of radiation that may be used in the methods of the invention include, but are not limited to, external beam radiotherapy (EBRT or XRT) or teletherapy, brachytherapy or sealed source radiotherapy, systemic radioisotope therapy or unsealed source radiotherapy.

In accordance with one or more embodiments of the methods of the present invention, the NLSC can be administered to the subject via any number of routes which allow administration of viable cells, including, for example, intravenous, intrathecal, local and intra-tumor injection, implants, systemic, parenteral, subcutaneous, intravascular, intramuscular, intraperitoneal, topical, transdermal, buccal, intravaginal, ocular, inhalation, depot injection, and through various medical devices.

With respect to NLSC methods described herein, a pharmaceutically acceptable carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers which can be physiologically acceptable (e.g., phosphate buffer) as well as solid compositions such as solid-state carriers or latex beads.

The carriers or diluents used herein may be solid carriers or diluents for solid formulations, liquid carriers or diluents for liquid formulations, or mixtures thereof.

Solid carriers or diluents include, but are not limited to, extracellular matrix, any scaffolds, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, or suspensions. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

The choice of carrier will be determined, in part, by the particular NLSC compositions, as well as by the particular method used to administer the composition. Accordingly, there are a variety of suitable formulations of the pharmaceutical compositions of the invention. The following formulations for parenteral, subcutaneous, intravenous, intramuscular, intraarterial, intrathecal and interperitoneal administration are exemplary, and are in no way limiting. More than one route can be used to administer the NLSC compositions of the present invention, and in certain instances, a particular route can provide a more immediate and more effective response than another route.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

As used herein the term "pharmaceutically active compound" or "therapeutically active compound" means a compound useful for the treatment or modulation of a disease or condition in a subject suffering therefrom. Examples of pharmaceutically active compounds can include any drugs known in the art for treatment of disease indications. A particular example of a pharmaceutically active compound is a chemotherapeutic agent.

The term "chemotherapeutic agent" as well as words stemming therefrom, as used herein, generally includes pharmaceutically or therapeutically active compounds that work by interfering with DNA synthesis or function in cancer cells. Based on their chemical action at a cellular level, chemotherapeutic agents can be classified as cell-cycle specific agents (effective during certain phases of cell cycle) and cell-cycle nonspecific agents (effective during all phases of cell cycle). Without being limited to any particular example, examples of chemotherapeutic agents can include alkylating agents, angiogenesis inhibitors, aromatase inhibitors, antimetabolites, anthracyclines, antitumor antibiotics, monoclonal antibodies, platinums, topoisomerase inhibitors, and plant alkaloids.

In accordance with an embodiment, the present invention can include a composition wherein the chemotherapeutic agent is administered to the subject either before, or after localization of the NLSC using the methods of the present invention.

The dose will be determined by the efficacy of the particular formulation and the location of the target population of cells in the subject, as well as the body weight of the subject to be treated. In accordance with an embodiment, the amount of NLSC administered to a subject during a round of treatment is between about $1 \times 10^5$ cells to about $1 \times 10^{10}$ cells.

With regard to the chemotherapeutic agents used in accordance with one or more embodiments of the present invention, typically, an attending physician will decide the dosage of the composition with which to treat each individual subject, taking into consideration a variety of factors, such as age, body weight, general health, diet, sex, compound to be administered, route of administration, and the severity of the condition being treated. By way of example, and not intending to limit the invention, the dose of the compositions of the present invention can be about 0.001 to about 1000 mg/kg body weight of the subject being treated, from about 0.01 to about 100 mg/kg body weight, from about 0.1 mg/kg to about 10 mg/kg, and from about 0.5 mg to about 5 mg/kg body weight. In another embodiment, the dose of the compositions of the present invention can be at a concentration from about 1 nM to about 10,000 nM, preferably from about 10 nM to about 5,000 nM, more preferably from about 100 nM to about 500 nM.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

It is contemplated, in accordance with the present invention, that in an embodiment, the NLSC of the present invention comprise a targeting agent. By "targeting agent" is meant any object that enables specific interaction with a target. The targeting agent can migrate and integrate into a defined target tissue or population of cells, for example, in response to signaling from the target cell population. For example, growing tumor expresses cytokines (growth factors EGF, VEGF, TGF, etc.). Cell-surface molecules that are cancer specific antigens (or disease-specific antigens) can also serve as targets.

EXAMPLES

Cell Culture. Murine mesenchymal stem cell lines were obtained from the Tulane University Center for Gene Therapy under Material Transfer Agreement. These cells were originally derived from femurs and tibiae of C57BL/6 mice with or without constitutively expressed green fluorescent protein (GFP) (transgenic C57tgGFP). The majority of experiments were performed using GFP-expressing murine mesenchymal stem cells. Cells were grown in Iscov's Modified Dulbecco Medium (Invitrogen/GIBCO, CA) that was supplemented with 10% Premium Select fetal calf serum (FCS, Atlanta Biologicals, GA), 10% equine serum (ES, Hyclone, Utah), 100 U/mL penicillin, and 100 μg/mL streptomycin (Invitrogen, CA). Cells were cultured in T75 flasks and passaged two or three times after thawing before labeling. Cells were split twice a week (to an approximate cell density of 5-7×$10^5$ cells per flask). Cell proliferation, colony formation and differentiation assays were performed with cells according to the instructions shipped with cells.

Assessment of toxic effects due to cell loading with NP and AMF exposure was performed by Trypan Blue exclusion as a measure of cell viability/immediate cell death rates. Long-term effects of the cell loading with the BNF-particles were studied after washing the cells and continued incubation in iron-free medium (for up to 3 weeks after loading) and compared with unlabeled controls (clonogenic assay). Inhibition of proliferation was used as all additional measure for potentially toxic effects. For cell proliferation and colony formation assays, cells were washed with PBS, harvested by trypinization, resuspended in complete growth medium) and plated in 24 well plates (3×$10^5$ or 1-300×$10^2$ cells/well, respectively). Cell counting was performed after 24, 48, 72, and 96 hours of incubation. Colonies were counted 2 weeks after cell plating.

For differentiation assay, cells were plated at low density (1×$10^3$/well in 6-well tissue culture plates), grown for 10 days with weekly medium change, and then incubated for 3 weeks in osteogenic (containing 1 nM Dexamethasone, 20 mM β-glycerophosphate, 50 μM L-ascorbic acid 2-phosphate sesquimagnesium salt, 50 ng/ml L-thyroxine sodium pentahydrate) or adipogenic (containing 5 μg/ml insulin, 50 μM indomethacin, 1 μM dexamethasone, 0.5 μM 3-isobutyl-1-methylxanthine) differentiation media with medium change twice a week, and then stained for 10 minutes with 2 ml of 40 mM Alizarin red (pH 4.1; Sigma) for mineral deposits or Oil Red-O (Sigma, Inc. St Louis, Mo.) for fat globules.

Iron oxide loading. Cell loading with iron oxide was performed by overnight incubation of cells with BNF particles (Micromod Partikeltechnologie, GmbH, Rostock, Germany). Cells were kept in culture 24 hours after passaging before the BNF particles were added. Briefly, cells were grown in T175 flasks, and 50 μl of BNF particles (1% solids) and 10 μl PLL (PLL; R&D Systems, Minneapolis, Minn., USA) were added to 20 ml of the complete growth medium. Loading was performed by co-incubation of the iron oxide BNF particles in the cell culture medium for 24 hours. After the loading procedure, cells were washed three times with phosphate-buffered saline (PBS without $Mg^{2+}$ and $Ca^{2+}$, Gibco, USA), and fresh medium was added. The efficiency of cell loading and iron oxide retention time was determined by in vitro Prussian Blue staining, by photometry (absorbance at 490 nm), and by inductively coupled-Mass Spectroscopy of cells taken at different time points up to one month post loading.

Nanoparticles. The starch coated BNF-particles have been described as core-shell particles in which the core is magnetite (>98%) with measured magnetization saturation, Ms=(41.08±0.03) kA m2 g-1, mean diameter~44 nm, and comprised of an aggregate of several ~20 nm magnetite parallelepiped-shaped crystals. BNF particles have unique characteristics, in that they become heated when exposed to an AMF.

In a separate experiment, cells were loaded by incubation with the clinically used contrast agent Feridex (Advanced Magnetics, Inc. Cambridge, Mass., USA, mean diameter 100 nm, total iron content 11.2 mg Fe/ml). Feridex® is a superparamagnetic contrast agent for MRI, an application for which increased heating efficiency is unnecessary (I. Bayer HealthCare Pharmaceuticals, Feridex® Prescribing Information. 2007). The particles comprise iron oxide crystals with 4-10 nm diameter embedded in a dextran matrix that have a non-stoichiometric composition of FeO.

Inductively-Coupled Mass Spectroscopy. For mass spectroscopy, cell samples were weighed and then transferred to microwave digestion vessels. Then 1 ml of optima grade $HNO_3$ (Fischer Scientific, Pittsburgh, Pa.) was added to each sample and to sample preparation blanks, and the samples were microwave digested (Mars 5, CEM Corporation, Matthews, N.C.). Upon cooling, the samples were diluted to 2% in polystyrene test tubes (Sarstedt, Nümbrecht, Germany)

and an internal standard of scandium was added to a concentration of 0.05 ng/ml. Analyses of diluted sample digests were carried out using inductively-coupled (ICP) mass spectroscopy (Agilent 7500ce, Agilent Technologies, Inc., Columbia, Md.).

Sample Preparation. Sample digestion was conducted by microwave digestion using a MARSS Xpress microwave (CEM Corporation, Matthews N.C.). Each cell sample was transferred to a 7 ml Teflon microwave digestion vessel (Savillex Corporation, Eden Prairie Minn.) and 1 ml of optima grade $HNO_3$ (Fisher Scientific, Columbia, Md.) was added. The 7 ml Teflon digestion vessel was sealed and placed into a 55 ml Teflon microwave digestion vessel (CEM Corporation, Matthews, N.C.) and 10 ml of ultra-pure $H_2O$ (Millipore Corporation, Billerica, Mass.) was added to the larger digestion vessel to assist in the microwave digestion. The 55 ml Teflon microwave digestion vessel was sealed and assembled according to manufacturer's protocol. A two stage ramp-to-temperature microwave method was followed: 15 minutes ramp to 165° C., followed by a 7 minutes ramp to 175° C. with a hold of 30 minutes.

Upon cooling, samples were removed from the microwave and diluted for Fe analysis by ICP-MS. 100 µl of sample digest was added to 4.900 ml of ultra-pure $H_2O$ to achieve a final $HNO_3$ concentration of 2%. Internal standard, Sc, (CPI Incorporated, Santa Rosa, Calif.) was added to achieve a final concentration of 50 µg/1 to monitor instrument drift during analysis time. For every batch of 21 cell samples, 3 samples of NIST standard reference material (SRM) 2709 San Joaquin Soil (NIST, Gaithersburg, Md.) were digested and analyzed, as well as 3 reagent blanks were digested and analyzed for quality control.

Sample Analysis. Total Fe content of the cell samples was performed using an Agilent 7500ce Inductively Coupled Plasma Mass Spectrometer (Agilent Technologies, Santa Clara, Calif.). An eight point calibration curve (0, 1, 5, 10, 50, 100, 500, 1000 µg/l) was performed. Total Fe content of each cell sample was calculated to account for dilutions during sample preparation, blank corrected using the average Fe value of the reagent blanks, and adjusted based upon the recovery of Fe from SRM 2709. The analytical limit of detection (LOD), as calculated by 3 times, the standard deviation of the lowest detectable calibration standard (1 µg/l) was determined. For the samples with the values that were below the analytical LOD, ½ the LOD was substituted.

AMF exposure and irradiation. After BNF-labeling, NLSC suspensions or monolayers were exposed to an AMF. The AMF system comprised three main components: (a) the power source, (b) an external impedance matching (capacitance) network; and, (c) an inductor. The power supply was an 80 kW induction heating system manufactured by PPECO (Watsonville, Calif.) that provides an alternating current to a resonant circuit with variable frequency between 135 kHz and 400 kHz. The external impedance match network (AMF Life Systems, Inc., Auburn Hills, Mich.) was adjusted for stable oscillation at 160±1 kHz with a total capacitance of 1.33 µF with five 0.2 µF and one 0.33 µF capacitors, each rated to provide up to 400 A at 1 kV. The load comprised an inductor, or a four-turn solenoid with inner diameter of 45.5 mm, outer diameter of 57.5 mm, and a length of 32 mm Measurements of the AMF amplitude were taken in the center of the coil with a magnetic field probe that measures magnetic flux lines in two orthogonal dimensions.

Cells were exposed to the 600 Gauss (G), 800G, and 1100G AMF in polystyrene tubes (BD Falcon, Bedford, Mass., USA) or 60 $mm^2$ culture dishes (Corning, N.Y., USA), respectively. Sample temperatures were measured with fiber optic probes (FISO Technologies, Quebec City, Canada) in a separate tube (plate) under similar conditions with the same cell concentration. Temperatures were recorded at one-second intervals, beginning after samples were in place for about thirty seconds before AMF exposure.

After 20 minutes of AMF exposure, cells were re-suspended and plated in triplicates in 24-well plates for viability and proliferation assessment and for the clonogenic assay or in 6 well plates for differentiation assay. In one group of experiments, immediately after AMF exposure, cells were irradiated with photons ($Cs^{137}$ Gammacell 40, Nordion, Ottawa, Ont., Canada), at approximately 0.5 Gy/min for 10 minutes (total of 5 Gray). After 24, 48, 72, and 96 hours, cells were stained with 0.1% Trypan Blue and counted. Cell colonies were counted two weeks after AMF exposure and irradiation.

MRI Studies. For MRI studies, NLSC were loaded with BNF particles (with or without Poly-L-Lysine), washed in PBS, counted, and re-suspended in 2% Agarose (Type XI, Sigma Chemical. Co.) to create phantoms containing loaded cells in PCR tubes (Denville Scientific Inc., Metuchen, N.J., USA). MR images were acquired with Bruker Biospec 9.4T system with the following parameters: echo time=8, 12, and 16 ms; repetition time=500 ms; field of view=32×32 mm; matrix size=128×80. MR images were analyzed, and reconstructed with IDL program (ITT Visual Information Solutions) and ImageJ (National Institutes of Health).

Example 1

Figure 1B:
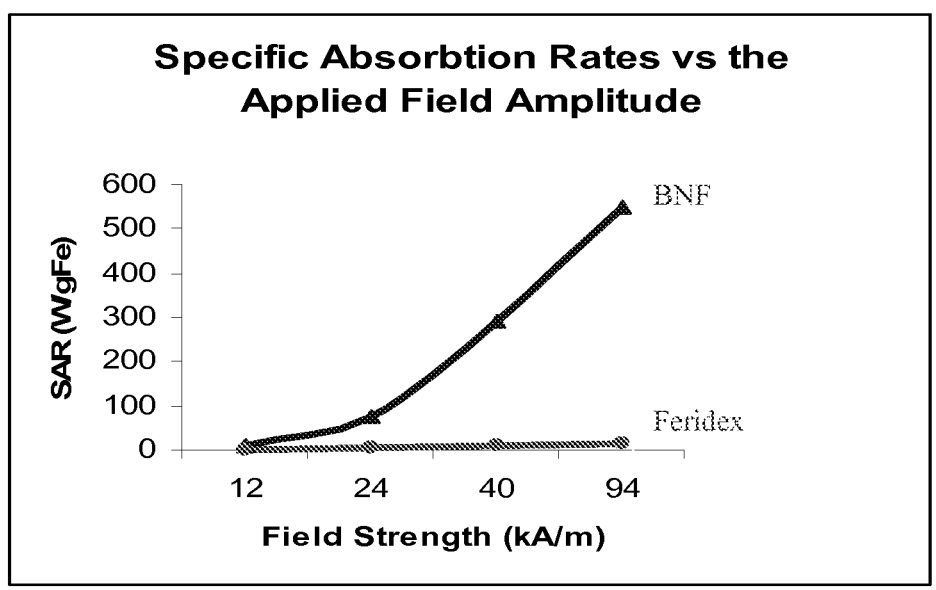
FIG. 1B is a plot of data for two particles studied in W/gFe vs. the applied field amplitude.

Particle heating and loading characteristics. BNF particles have unique characteristics including that they heat in an AMF. FIG. 1 demonstrates the heating rates of the BNF particles as a function of AMF amplitude. The magnetic field amplitude (peak-to-peak) in Oersteds is a measure of power of the magnetic field. Higher power (higher field amplitude and more intense magnetic flux density) extracts more heat from the particles.

Figure 2A:
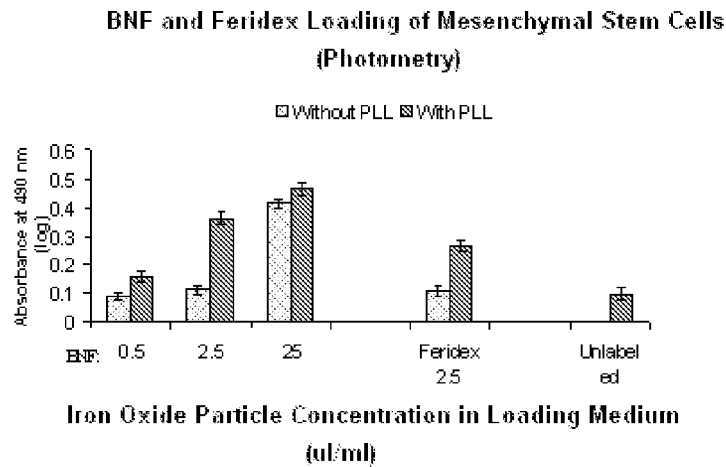
FIG. 2 A-C are graphs depicting the effect of differing labeling conditions on iron content in NLSCs (Photometry and ICP-Mass Spectroscopy data).
Figure 2B:
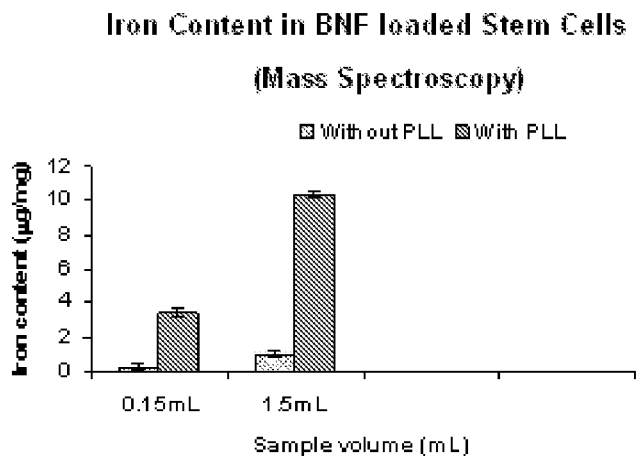
Figure 2C:
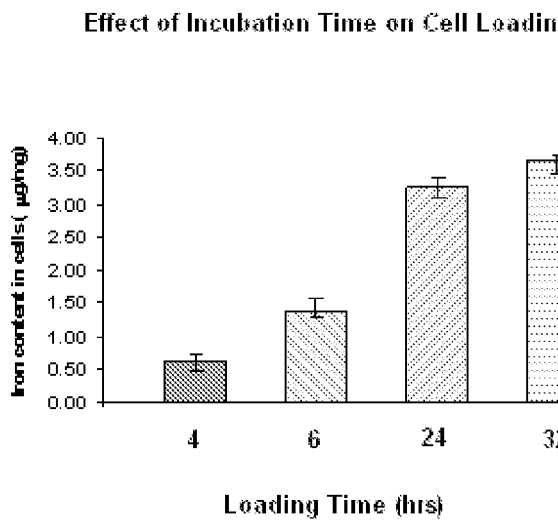

To test the hypothesis that stem cells can be efficiently loaded with bi-functional BNF particles for imaging and hyperthermia, we examined loading characteristics and optimized loading conditions for mouse mesenchymal stem cells with BNF-particles (FIG. 2). According to ICP-mass spectrometry results (FIG. 2B), iron cell load varied from 0.6 to 1.6 pg/cell after overnight cells loading with BNF particles (2.5 µl/ml concentration in growth media). Loading of MSC with Feridex resulted in iron concentrations of 1-5 pg iron per cell. Iron content per cell increased to 7-23 pg Fe/cell when cells were loaded with BNF particles in the presence of PLL (0.5 µl/ml) (FIG. 2B). During cell incubation in growth media containing BNF-particles and PLL, we observed increasing NP accumulation during 4-32 hrs (FIG. 2C). There was no significant increase in iron uptake after 24 hours, thus, this time (overnight incubation) was chosen as an optimal loading time.

Example 2

Figure 3:
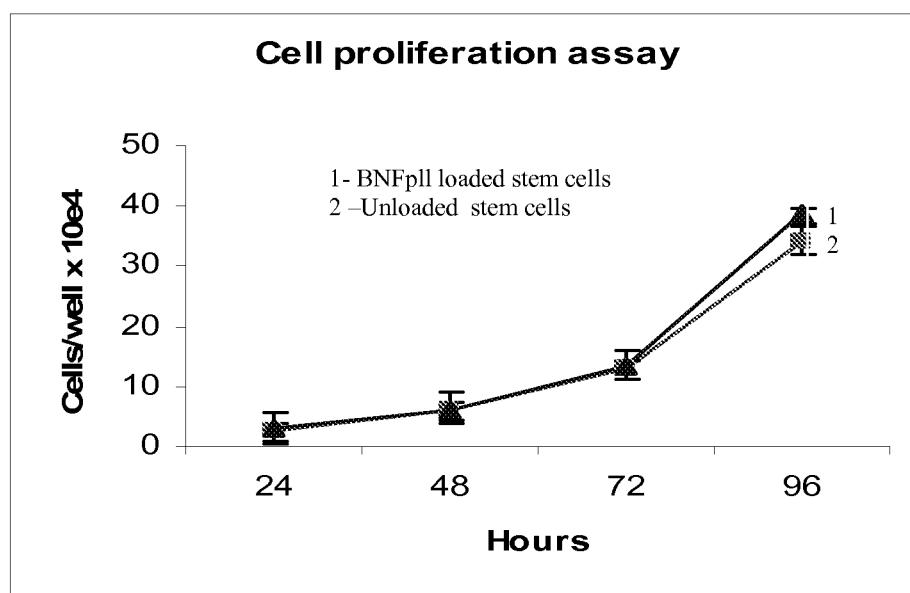
FIG. 3 is a graph depicting the proliferation assay for the BNF(PLL)-loaded mouse mesenchymal stem cells; 1—unloaded cells; 2—BNF(PLL)-loaded cells (cell loading in the presence of Poly-L-Lysine (PLL)).

Cell survival, proliferation, differentiation. The effect of loading with the BNF particles on NLSC survival and growth was examined by using the Trypan Blue exclusion method which demonstrates cell viability. Viable cells were calculated after overnight cell loading with the BNF particles. Cells were re-suspended in the complete growth medium and plated in 24-well plates (in triplicates) for cells proliferation assay. Count of viable cells after 24, 48, 72, and 96 hours demonstrated that mouse mesenchymal stem cells can be efficiently loaded with iron-oxide BNF-particles without disturbing their viability and proliferation potential (FIG. 3A).

Standard differentiation assay also demonstrated that BNF-loaded cells can differentiate into adipocytes and osteocytes as unloaded control cells, so their differentiation potential also was not altered by BNF-labeling (data not shown). That suggests that BNF-loaded NLSC are capable to differentiate accordingly to microenvironment after internalizing the particles, suggesting they can participate in tumor neovasculogenesis.

Example 3

Figure 4:
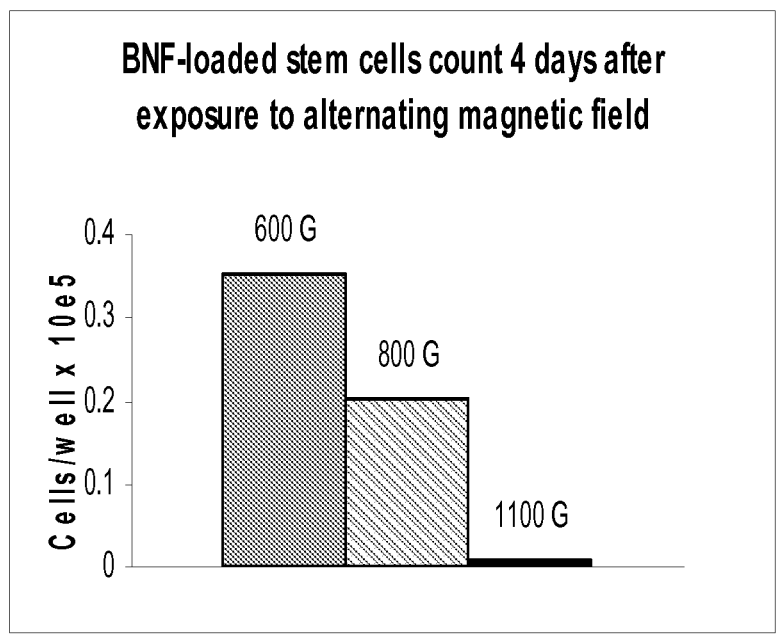
FIG. 4 is a graph depicting NLSC survival after exposure to AMF 600, 800, and 1100 Gauss. Count of unlabeled cells exposed to AMF at the same conditions was $3.9 \times 10^5$/well+ $0.03 \times 10^5$.

Effect of AMF. To examine sensitivity of BNF-loaded NLSC to AMF, cells suspensions were exposed to 600, 800, and 1100 Gauss AMF for 20 minutes. In these experiments temperature (measured in a separate tube with the same loaded cells concentration) raised maximum to 44.3° C. (at 1100 G). BNF-loaded cells were sensitive to AMF in a dose-dependent manner. The fraction of surviving cells after exposure to AMF was extremely low in comparison to control unloaded cells: 9% after 600G exposure, 5% after 800G, and 0.4% after 1100G AMF (FIG. 4A). Average count of unloaded cells exposed to AMF at the same conditions was $3.9\times10^5$/well.

Two weeks after 800 G AMF exposure, surviving BNF-loaded NLSC formed colonies (data not shown), while control cells (unloaded or BNF-loaded unexposed to AMF) were confluent by day 4 and detached from the surface after one week. NLSC colony forming ability was significantly reduced if cells exposed to AMF were subsequently exposed to gamma-irradiation at 5 Gy. BNF-loaded cells that were not exposed to AMF and exposed to 5 Gy and unloaded cells treated with AMF and 5 Gy resulted in an ~50% decrease in cells survival (data not shown).

Example 4

Figure 5:
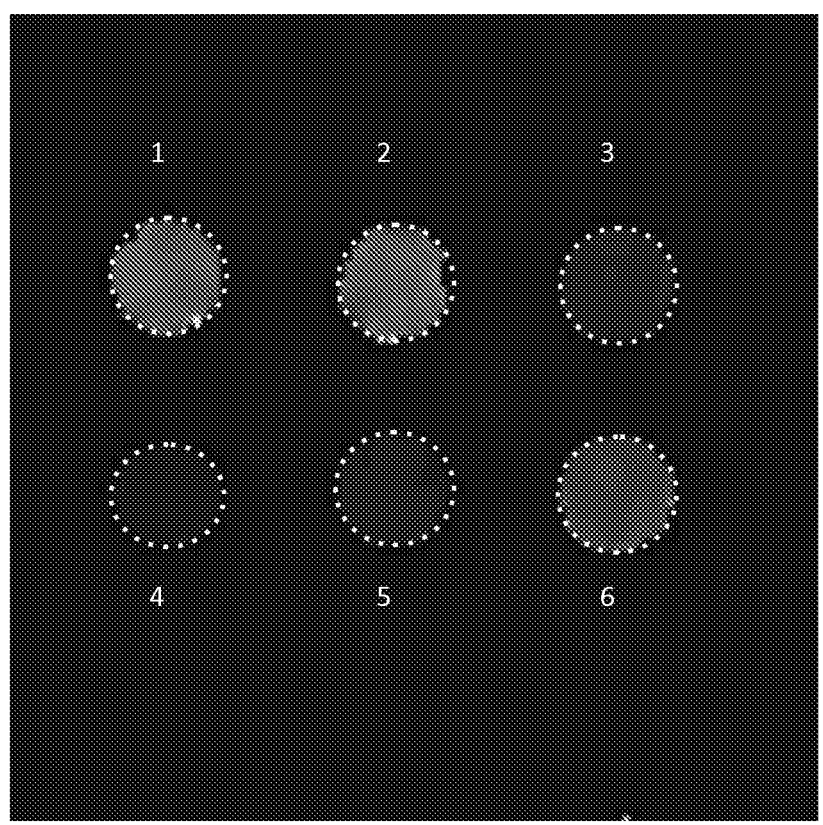
FIG. 5 is a $T_2$* map of BNF-loaded stem cells in 2% agarose. 1—Unlabeled cells; 2—Unlabeled cells with PLL; 3—BNF-labeled cells ($2 \times 10^6$); 4—BNF(PLL)-labeled cells ($2 \times 10^6$); 5—BNF(PLL)-labeled cells ($1 \times 10^6$); 6—BNF (PLL)-labeled cells ($2 \times 10^5$). Each $T_2$* value obtained was 40.0, 41.2, 10.9, 5.9, 9.1, 23.6 ms, respectively.
Figure 6:
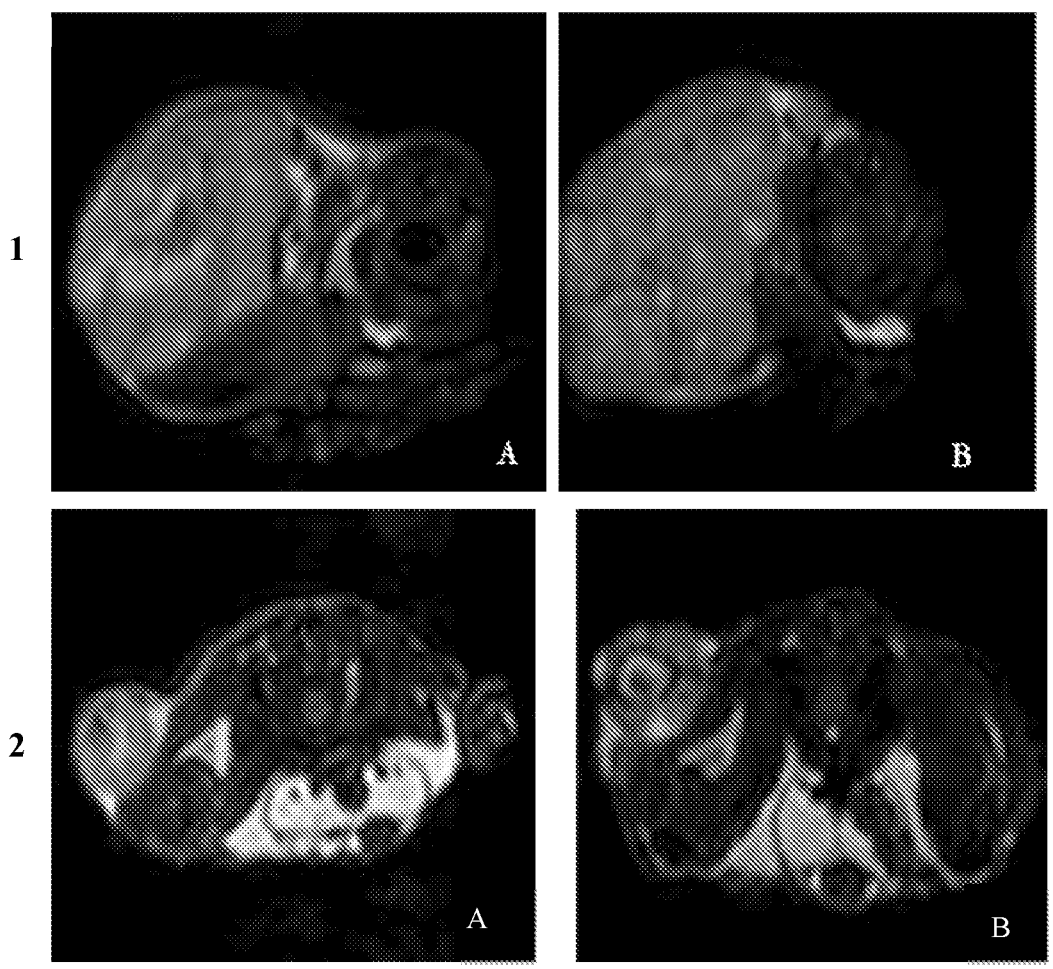
FIG. 6 demonstrates homing of NLSC to tumors. The pictures demonstrate in vivo MR imaging ($T_2$*; 9.4T) of prostate cancer (PC3) tumor xenografts in mice (A) before and (B) one week after intravenous injection of 1—BNF-particles or 2—BNF-loaded stem cells.
Figure 7:
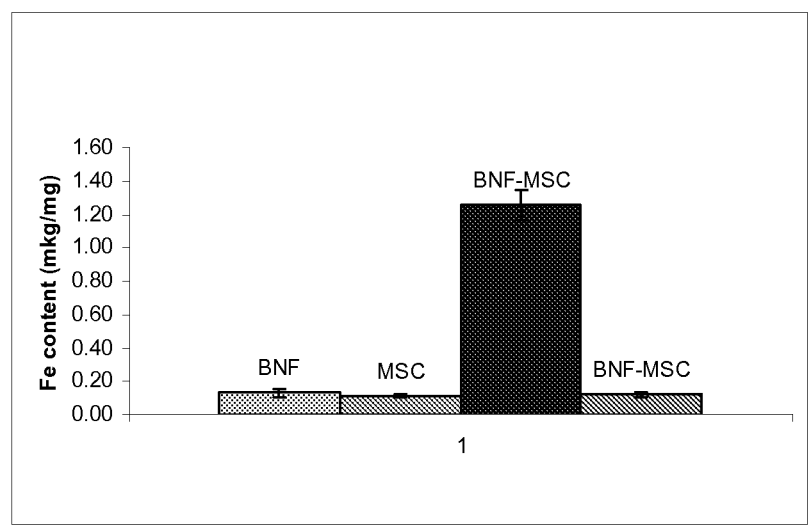
FIG. 7 is a graph depicting Iron accumulation in PC3 tumors and normal tissue 5 days after intravenous injection of BNF particles, stem cells, or BNF-loaded stem cells (ICP-Mass Spectroscopy data).

Imaging characteristics. Monitoring the location and migration of grafted cells is essential for understanding their interaction within the host and their therapeutic effects. Magnetic resonance imaging (MRI) can study these processes non-invasively. Various strategies have been used for loading of stem and progenitor cells with iron oxide particles for their in vivo visualization by MRI. In these experiments, overnight incubation with iron oxide BNF-nanoparticles (NLSC) resulted in efficient cells loading and generating of a pronounced contrast in $T_2^*$-weighted images as shown in FIG. 5.

Poly-L-Lysine (PLL) was used to enhance accumulation and penetration of BNF particles in NLSC that resulted in efficient cell labeling for MRI. BNF-loaded cells were visualized due to their capacity to influence the magnetic susceptibility and thus reduce or even quench the signal intensity in $T_2$ and $T_2^*$-weighted MR images. Agar phantoms were also used with different cell concentrations (3D multi-slice multi-echo experiments) to obtain $T_2^*$-maps. Reconstructed MR images of BNF-loaded cell phantoms are shown in FIG. 5. BNF-loaded NLSC had shorter $T_2$ values compared to the control cells, indicating that BNF particles were successfully incorporated into NLSC. Cell loading with BNF particles in the presence of PLL reduced $T_2$ values even more than particles without PLL. Comparison with the known cell density confirms that single cells are detectable by high-resolution 3D MRI.

As provided herein, injected NLSC preferentially accumulated in the sites of neovasculogenesis, differentiated into endothelial cells, and participated in tumor vasculature formation. It appears that NLSC can direct the therapeutic heat to the vasculature of growing tumors minimizing both heat exposure and particle concentrations in surrounding tissues. In this manner, cytotoxic heat can be deposited specifically to the sites of neovascularization in the hypoxic areas within the tumors. Thus, the most radio- and chemo-resistant areas within the tumors can be targeted, and neovasculature can be destroyed by the exposure to AMF either alone or, more likely, in combination with other cancer treatment modalities. NLSC provide an additional opportunity to target hyperthermia (under MRI control) to the most radio- and chemo-therapy resistant hypoxic areas in tumors and to disrupt tumor vasculature after exposure to AMF (in combination with radio- and/or chemo-therapy).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating a tumor in a subject, comprising:
   a) administering intravenously to the subject an amount of mesenchymal stem cells loaded with bi-functional nanoferrite magnetic nanoparticles;
   b) allowing sufficient time for the mesenchymal stem cells loaded with the bi-functional nanoferrite magnetic nanoparticles to localize to the tumor; and, c) applying an alternating magnetic field to the subject and heating the bi-functional nanoferrite magnetic nanoparticles loaded into the mesenchymal stem cells localized to the tumor, thereby heating the tumor in the subject.

2. The method of claim 1, wherein the bi-functional nanoferrite magnetic nanoparticles comprise a core of 75-80% (w/w) magnetite.

3. The method of claim 1, wherein the mesenchymal stem cells comprise stem cells selected from the group consisting of autologous stem cells and allogenic stem cells.

4. The method of claim 3, wherein the autologous stem cells are selected from the group consisting of: a) cells derived from circulation or endothelial progenitor cells; b) cells derived from bone marrow; and c) cells obtained from cell banks.

5. The method of claim 3, wherein the allogenic stem cells are selected from the group consisting of: a) cells derived from non-embryonic tissues or adult stem cells; and b) cells derived from human embryonic stem cell (hESC) lines from in vitro fertilization (IVF) embryos.

6. The method of claim 1, further comprising: detecting the tumor by imaging the mesenchymal stem cells loaded with the bi-functional nanoferrite magnetic nanoparticles localized at the tumor through magnetic resonance imaging (MRI) before step c).

7. The method of claim 1, wherein the amount of mesenchymal stem cells is between $1 \times 10^3$ to $1 \times 10^{11}$ cells.

8. The method of claim 1, wherein the sufficient time for the mesenchymal stem cells to localize to the tumor is between 3 days to 10 days.

9. The method of claim 1, wherein the magnetic field strength of the alternating magnetic field administered to the subject is between 500 Gauss to 1500 Gauss.

10. The method of claim 9, wherein the magnetic field amplitude of the alternating magnetic field is between 5 Oe to 1000 Oe.

11. The method of claim 1, wherein the tumor is a solid tumor.

12. The method of claim 1, wherein the tumor is a primary tumor.

13. The method of claim 1, wherein the tumor is a metastatic tumor.

14. The method of claim 1, further comprising: administering a pharmaceutical composition comprising one or more chemotherapeutic agents before or after the mesenchymal stem cells loaded with the bi-functional nanoferrite magnetic nanoparticles are localized at the tumor.

15. The method of claim 14, further comprising: administering an effective amount of radiotherapy to the tumor.

16. The method of claim 1, further comprising: administering an effective amount of radiotherapy to the tumor.

17. The method of claim 1, further comprising: detecting the tumor by imaging the mesenchymal stem cells loaded with the bi-functional nanoferrite magnetic nanoparticles localized at the tumor through magnetic resonance imaging (MRI) before step c).

* * * * *